(12) United States Patent
Suchkov et al.

(10) Patent No.: US 11,883,098 B2
(45) Date of Patent: Jan. 30, 2024

(54) DEVICE AND METHOD FOR DETERMINING AT LEAST ONE OCULAR ABERRATION

(71) Applicant: Carl Zeiss Vision International GmbH, Aalen (DE)

(72) Inventors: Nikolai Suchkov, Kusterdingen (DE); Siegfried Wahl, Donzdorf (DE)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 18/068,566

(22) Filed: Dec. 20, 2022

(65) Prior Publication Data

US 2023/0131746 A1 Apr. 27, 2023

Related U.S. Application Data

(63) Continuation of application No. PCT/EP2021/067113, filed on Jun. 23, 2021.

(30) Foreign Application Priority Data

Jun. 24, 2020 (EP) .................................... 20181916

(51) Int. Cl.
*A61B 3/10* (2006.01)
*A61B 3/00* (2006.01)
(Continued)

(52) U.S. Cl.
CPC .......... *A61B 3/1015* (2013.01); *A61B 3/0091* (2013.01); *A61B 3/12* (2013.01); *A61B 3/14* (2013.01); *G02C 7/027* (2013.01)

(58) Field of Classification Search
CPC ....... A61B 3/1015; A61B 3/0091; A61B 3/12; A61B 3/14; A61B 3/103; A61B 3/0025; G02C 7/027
(Continued)

(56) References Cited

U.S. PATENT DOCUMENTS 7,084,986 B2 * 8/2006 Hellmuth ............. A61B 3/1005
356/497
2003/0071969 A1 4/2003 Levine et al.
(Continued)

FOREIGN PATENT DOCUMENTS

EP 0156453 A1 10/1985
WO 2006/069725 A1 7/2006

OTHER PUBLICATIONS

Thibos et al., "Power Vectors: An Application of Fourier Analysis to the Description and Statistical Analysis of Refractive Error", Optometry and Vision Science, vol. 74, No. 6, pp. 367-375, Jun. 1997.

(Continued)

*Primary Examiner* — Mohammed A Hasan
(74) *Attorney, Agent, or Firm* — Tautz & Schuhmacher LLC; Georg M. Hasselmann

(57) ABSTRACT

A device and a method for determining an ocular aberration of at least one eye of a user are disclosed. The device contains a wavefront sensing unit for measuring at least one optical wavefront with at least one light beam, from which an ocular aberration of the at least one eye of the user is determined. The device further contains at least one diffractive element for generating multiple diffraction orders in the light beam in two meridians in a manner that the multiple diffraction orders are spatially separated on the wavefront sensing unit and in the eye of the user. The device and the method allow generating an ocular defocus map in a one-shot assessment in real-time, especially by employing an automated measurement of the ocular aberrations with regard to different eccentricities of the eye of the user in two meridians.

26 Claims, 7 Drawing Sheets

(51) Int. Cl.
*A61B 3/12* (2006.01)
*A61B 3/14* (2006.01)
*G02C 7/02* (2006.01)

(58) Field of Classification Search
USPC .......................................................... 351/206
See application file for complete search history.

(56) References Cited

U.S. PATENT DOCUMENTS

| | | | |
|---|---|---|---|
| 2003/0117581 A1 | 6/2003 | Martino et al. | |
| 2003/0214647 A1 | 11/2003 | Horwitz et al. | |
| 2004/0061830 A1 | 4/2004 | Hellmuth et al. | |
| 2005/0105044 A1 | 5/2005 | Warden et al. | |
| 2005/0195364 A1* | 9/2005 | Dai | A61F 9/00806 351/205 |
| 2007/0091263 A1* | 4/2007 | Chernyak | A61B 3/1015 351/205 |
| 2009/0161090 A1* | 6/2009 | Campbell | G01B 11/25 351/212 |
| 2011/0149230 A1* | 6/2011 | Menezes | G02C 7/048 351/159.16 |
| 2016/0073868 A1* | 3/2016 | Raymond | A61B 3/103 351/246 |

OTHER PUBLICATIONS

Lundström et al., "Unwrapping Hartmann-Shack images from highly aberrated eyes using an iterative B-spline based extrapolation method", Optometry and Vision Science, vol. 81, No. 5, pp. 383-388, May 2004.

Wei et al., "Design and validation of a scanning Shack Hartmann aberrometer for measurements of the eye over a wide field of view", Optics Express, vol. 18, No. 2, pp. 1134-1143, 2010.

Industrial Norm "Ophthalmic optics—Spectacle lenses—Vocabulary (ISO 13666:2019)", German and English version EN ISO ISO 13666:2019, Dec. 2019.

International Search Report and Written Opinion issued in PCT/EP2021/067113, to which this application claims priority, dated Sep. 16, 2021.

International Preliminary Report on Patentability issued in PCT/EP2021/067113, to which this application claims priority, dated Mar. 25, 2022.

Office Action by the Chinese Patent Office (SIPO) issued in CN 202180045001.6, which is a counterpart hereof, dated May 25, 2023, and English translation thereof.

* cited by examiner

DEVICE AND METHOD FOR DETERMINING AT LEAST ONE OCULAR ABERRATION

CROSS REFERENCE TO RELATED APPLICATIONS

This application is a continuation application of international patent application PCT/EP2021/067113, filed on Jun. 23, 2021, which claims priority to European patent application EP 20 181 916.6, filed on Jun. 24, 2020, both of which are hereby incorporated by reference in their entireties.

TECHNICAL FIELD

The present disclosure relates to a device, a method, and a computer program product for determining at least one ocular aberration of at least one eye of a user as well as to a related method for producing at least one spectacle lens for the at least one eye of the user.

BACKGROUND

Devices, methods, and computer program products for determining at least one ocular aberration of at least one eye of a user are known. As generally used, the term "ocular aberration" refers to a difference between a surface of an ideal optical wavefront and a surface of an actual optical wavefront which is determined for the at least one eye of a user. Herein, the term "optical wavefront" relates to a surface which is perpendicular to a beam along which light propagates. Within a typical human population, the ocular aberration, usually, comprises at least one second-order spherocylindrical focus error, also denoted as "refractive error," wherein, however, at last one higher-order aberration may also occur.

According to X. Wei & L. Thibos (2010), *Design and validation of a scanning Shack Hartmann aberrometer for measurements of the eye over a wide field of view*, Optics Express, 18(2), 1134, doi.org/10.1364/oe. 18.001134, peripheral vision and off-axis aberrations do not only play an important role in daily visual tasks but may also influence eye growth and refractive development. Thus, they indicate that it is important to measure off-axis wavefront aberrations of human eyes objectively. To achieve efficient measurement, the authors incorporated a double-pass scanning system into a Shack Hartmann wavefront sensor (SHWS) in order to obtain a scanning Shack Hartmann aberrometer (SSHA). Herein, the prototype SSHA could, successfully, be employed to measure the off-axis wavefront aberrations over ±15° visual field within 7 seconds. In two validation experiments with a wide-angle model eye, the prototype measured change in defocus aberration accurately (<0.02 µm, 4 mm pupil) and precisely (<0.03 µm, 4 mm pupil).

In particular, for incorporating the double-pass scanning system into the SHWS, a lenslet plane of SHWS and scanning axes of X-Y scanning mirrors are co-aligned optically onto planes conjugated with the entrance pupil of the tested eye. For this purpose, three optical relay telescopes are used in a fashion that in the incoming optical path, the scanning axes of scanning mirrors form a scanning center via one of the optical relay telescopes, which is further conjugated with the entrance pupil center of the eye via a further of the optical relay telescopes. A spatially filtered and collimated narrow laser beam is introduced via a beam splitter which intersects with the scanning axes of the scanning mirrors and the entrance pupil center of the eye. As the scanning mirrors rotate, the laser beam rotates about a pivot point located at the center of the eye's entrance pupil, thereby injecting the laser beam along a different line-of-sight as specified in angular dimensions in object space. In the eye's image space, the laser beam scans across the retina and forms a sequence of retinal spots, wherein the scan pauses briefly (50 ms) to acquire an optical wavefront measurement. Thus, for each position of the scanning mirrors, the optical wavefront originating from the retinal spot is modulated by the ocular structures, in particular lens and cornea, and emerges at the entrance pupil. As the emerging optical wavefront propagates back, it is de-scanned by the scanning mirrors and, subsequently, sampled by an array of micro-lenses in the SHWS.

Despite the advantages of existing devices, methods, and computer program products for determining at least one ocular aberration of at least one eye of a user, there is still room for improvement. In particular, most existing devices and methods do not allow an automated measurement of the ocular aberrations of different eccentricities in two meridians. For systems with only a single scanning meridian, the eye of the user has to be moved in order to consecutively select the eccentricity in a particular meridian, thus, requiring an additional fixation of at least one target. For this purpose, the at least one target has to be placed at a distance of 5 meters or more in order to avoid accommodation, thus, placing constraints on the environment where the device and the method can be used. Moreover, a multiple fixation, usually, results in a prolonged measurement, thereby adding uncertainties to the measurement, in particular since a user wearing at least one lens may move with time, such that the ocular aberrations are, in general, modified across the field of view. Consequently, existing devices and methods can only by used by trained eye care professionals.

Although scanning systems exist which require a complicated and/or expensive optics, such as a rotational system around a pupil of the at least one eye of the user, a scanning system comprising at least one scanning galvo mirror, or the above-described scanning Shack Hartmann aberrometer, they do not offer a possibility of a one-shot measurement.

US 2005/0105044 A1 discloses wavefront measuring systems and methods which may be employed in detecting phase aberrations in a spectacle lens and in an eye. Various embodiments include disposing a modulation pattern in the path of a return beam from the spectacle lens or the eye, and imaging a diffraction pattern at a self-imaging plane relative to the modulation pattern with a detector. The diffraction pattern is analyzed and the results are used to produce a representation of the wavefront phase characteristics that describe aberrations in the lens or eye being measured. Illumination and processing techniques for improving the measurement results are disclosed. Various embodiments comprise systems adaptable to both measure aberrations in lenses in spectacles as well as in a patient's eyes.

US 2003/0214647 A1 discloses a wavefront measuring system and a method for detecting phase aberrations in wavefronts that are reflected from, transmitted through, or internally reflected within objects sought to be measured, e.g., optical systems, the human eye, etc. including placing a reticle in the path of a return beam from the object, and placing a detector at a diffraction pattern self-imaging plane relative to the reticle. The diffraction pattern is analyzed and results in a model of the wavefront phase characteristics. A set of known polynomials is fitted to the wavefront phase gradient to obtain polynomial coefficients that describe aberrations in the object or within the wavefront source being measured.

SUMMARY

In particular with respect to the disclosure of X. Wei & L. Thibos, see above, it is therefore an objective of the present disclosure to provide a method, a device and a computer program product for determining at least one ocular aberration of at least one eye of a user as well as a related method for producing at least one spectacle lens for the at least one eye of the user, which at least partially overcome the above-mentioned problems of the state of the art.

It is a particular objective of the present disclosure to enable an efficient assessment of a peripheral defocus, specifically, to be able to obtain a whole ocular defocus map in a one-shot measurement of the at least one eye of the user, especially, by employing an automated measurement of the ocular aberrations with regard to different eccentricities of the at least one eye of the user in two meridians.

More particular, it would, thus, be desirable to provide a diagnostic tool for evaluating myopia progression, especially for personalizing myopia control treatments in order to be able to provide personalized optical lenses, such as multifocal contact lenses or progressive spectacles or, especially, myopia progression management (MPM) lenses for peripheral defocus management or defocus incorporated multiple lens segment lenses (DIMS), based on a single and fast measurement of the peripheral defocus of the at least one eye of the user and/or in a continuous monitoring of changes induced by accommodation of the at least one eye of the user or a movement of at least one lens worn by the user.

This problem is solved by a device, a method and a computer program product for determining a refractive error of at least one eye of a user as well as a related method for producing at least one spectacle lens for the at least one eye of the user, wherein an ocular aberration of at least one eye of the user is determined from at least one optical wavefront. Exemplary embodiments, which might be implemented in an isolated fashion or in any arbitrary combination, are discussed below.

As used in the following, the terms "have," "comprise," or "include" or any arbitrary grammatical variations thereof are used in a non-exclusive way. Thus, these terms may refer to both a situation in which, besides the feature introduced by these terms, no further features are present in the entity described in this context and to a situation in which one or more further features are present. As an example, the expressions "A has B," "A comprises B," and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, as used in the following, the terms "preferably," "more preferably," "particularly," "more particularly," or similar terms are used in conjunction with optional features, without restricting alternative possibilities. Thus, features introduced by these terms are optional features and are not intended to restrict the scope of the claims in any way. The disclosure may, as the skilled person will recognize, be performed by using alternative features. Similarly, features introduced by "in an embodiment of the disclosure" or similar expressions are intended to be optional features, without any restriction regarding alternative embodiments of the disclosure, without any restrictions regarding the scope of the disclosure and without any restriction regarding the possibility of combining the features introduced in this way with other features of the disclosure.

In a first aspect, the present disclosure relates to a device for determining at least one ocular aberration of at least one eye of a user. As already indicated above, the term "ocular aberration" refers to a difference between a surface of an ideal optical wavefront and a surface of an actual optical wavefront which is determined for the at least one eye of a user. Herein, the term "optical wavefront" relates to a surface which is perpendicular to a beam along which light propagates. Instead of the term "user," a different term, such as "subject," "person," "test person," or "wearer of eye glasses," may also be applicable.

In accordance with the present disclosure, the device comprises at least:
  a wavefront sensing unit designated for measuring at least one optical wavefront comprised by at least one light beam, wherein an ocular aberration of the at least one eye of the user is determined from the at least one optical wavefront; and
  at least one diffractive element designated for generating multiple diffraction orders in the at least one light beam in two meridians in a manner that the multiple diffraction orders are spatially separated on the wavefront sensing unit and in the at least one eye of the user.

The present device for determining at least one ocular aberration of at least one eye of a user can, preferably, be used in a method for producing at least one of a spectacle lens or a contact lens for the at least one eye of the user as described below in more detail. Based on standard ISO 13666:2019, also referred to herein as the "standard," Section 3.5.2, each of the terms "spectacle lens" and "contact lens" relate to an optical lens which is used within the framework of the present disclosure for determining and/or correcting the at least one ocular aberration of at least one eye of a user, wherein the spectacle lens is carried in front of the eye of the user, while the contact lens is in direct contact with the eye of the user. Further, the term "glasses" refers to an arbitrary element which comprises two individual spectacle lenses and a spectacle frame, wherein each spectacle lens is prepared for being received by the spectacle frame selected by the user.

As further already indicated above, the ocular aberration within a typical human population, usually, comprises at least one second-order spherocylindrical focus error, also denoted as "refractive error." For describing a spherocylindrical lens which is designed for correcting a spherocylindrical focus error, various approaches are possible. As defined in the standard, Section 3.6.6, the term "spherocylindrical lens" refers to a spectacle lens having a spherical surface and a cylindrical surface. Further, the spherocylindrical lens is defined, according to Section 3.13.1, as a spectacle lens which combines a paraxial, parallel beam of light in two individual, mutually perpendicular focal lines, whereby the spectacle lens has an apex refractive power only in two meridians. Further, the term "apex refractive power" is, according to Section 3.10.7, defined as a reciprocal value of the width of the paraxial section. As further defined in Section 3.2.12 and 3.13.2, the term "meridian" relates to one of two perpendicular planes of the spectacle lens having an astigmatic effect being parallel to the two focal lines. Herein, the term "astigmatic effect" corresponds to an "astigmatic difference" which is defined in Section 3.13.6 as a difference between the value of the apex refractive power in the second meridian and the value of the apex refractive power in the first meridian. Further, the "cylindrical power" refers, according to Section 3.13.7, to an algebraic difference between the refractive values of the meridians, wherein the refractive value of a particular meridian being used as a reference is subtracted from the refractive value of the other meridian, while the "cylinder axis" indicates according to Section 3.13.8 the direction of the meridian of the spectacle lens whose apex refractive index is used as the reference.

As an alternative, L. N. Thibos, W. Wheeler and D. Horner (1997), *Power Vectors: An Application of Fourier Analysis to the Description and Statistical Analysis of Refractive Error*, Optometry and Vision Science 74 (6), S. 367-375, propose to approach the description of a spherocylindrical lens from a viewpoint of Fourier analysis of a power profile. They show that the familiar sine-squared law leads naturally to a Fourier series representation with exactly three Fourier coefficients, representing natural parameters of a thin lens. Herein, a constant term corresponds to a mean spherical equivalent (MSE) power, whereas amplitude and phase of the harmonic correspond to the power and axis of a Jackson cross-cylinder (JCC) lens, respectively. Expressing the Fourier series in rectangular form leads to the representation of an arbitrary spherocylindrical lens as sum of a spherical lens and two cross-cylinders, one at axis 0° and the other at axis 45°. The power of these three component lenses may be interpreted as (x, y, z) coordinates of a vector representation of the power profile. The power vector representation of a spherocylindrical lens can be used for numerical and graphical analysis of optometric data for problems involving lens combinations, comparison of different lenses, and statistical distribution of refractive errors.

Preferably, the presently presented device for determining at least one ocular aberration of at least one eye of a user may comprise a light source. As generally used, the term "light source" refers to a unit which is designated for generating at least one light beam, wherein the at least one light beam which is provided by the light source is guided along at least one optical path. As used herein, the term "light" refers to electromagnetic radiation in at least one of the visible spectral range or the infrared spectral range. As generally used, the term "visible spectral range" refers to electromagnetic radiation having a wavelength of 380 nm to 780 nm, whereas the term "infrared spectral range" relates to electromagnetic radiation having a wavelength above 780 nm to 1000 µm, wherein the visible spectral range or the "near infrared spectral range," which refers to electromagnetic radiation having a wavelength above 780 nm to 1.5 µm, may particularly be preferred. Further, the term "light beam" relates to a propagation of the light in form of at least one ray, wherein a direction of propagation of the at least one ray is, generally, denoted herein by the term "optical path," wherein the optical path may be modified by at least one optical element, in particular selected from a mirror, a beam splitter, or a diffractive element, such as an optical grating. As further indicated above, the term "optical wavefront" refers to a surface which is perpendicular to the direction of propagation of the at least one light beam.

Herein, the light source can, in general, be selected from any known monochromatic source. As generally used, the term "monochromatic" refers to a single wavelength or a small bandwidth of wavelengths selected from one of the above-indicated spectral ranges. For this purpose, a laser diode could, preferably, be used, in particular by virtue of its simplicity, easy availability and low expenses. As an alternative, a combination of a polychromatic source and a tunable or fixed bandwidth filter, or a combination of a supercontinuum source and a tunable or fixed bandwidth filter could, advantageously, also be used, wherein the term "supercontinuum" refers to laser light having a small bandwidth which, after transition through a non-linear optical medium, exhibits an extended bandwidth, whereof a small bandwidth of desired wavelengths can be selected by using the tunable bandwidth filter, thus, allowing an alteration of diffraction angles and efficiencies of peripheral beams as described below in more detail.

Further, the device for determining at least one ocular aberration of at least one eye of a user may, preferably, comprise at least one optical element which is designated for guiding the at least one light beam to the at least one eye of the user and to a wavefront sensing unit. Herein, the at least one optical element may, preferably, be or comprise a combination of at least one optical relay system as described below in more detail and a beam splitter. As generally used, the term "beam splitter" relates to a particular kind of optical element which is designated for splitting a light beam into at least two, preferably exactly two, partial light beams. Herein, the beam splitter can, in general, be selected from any known beam splitter, in particular from a glass plate with dielectric coating, a dichroic mirror, a pellicle beam splitter, a beam splitter plate, or a polarizing beam splitter, such as a Wollaston prism, or a polarization grating. However, further kinds of beam splitters may also be feasible. For the purposes of the present disclosure, the beam splitter can be placed in the at least one optical path in a fashion that it may split the least one light beam as provided by the light source into at least two partial light beams, wherein at least one partial light beam may be guided to the at least one eye of the user and, after being reflected by the at least one eye of the user received from the eye of the user, especially, guided towards a wavefront sensing unit as described below in more detail.

In accordance with the present disclosure, the device for determining at least one ocular aberration of at least one eye of a user comprises a wavefront sensing unit. As generally used, the term "wavefront sensing unit" refers to an optical sensor which is designated for measuring the aberrations of an optical wavefront, wherein the term is, usually, applied to an optical sensor which does not require interference with a reference beam having no aberrations. Herein, the wavefront sensing unit may, preferably be selected from at least one of: a Shack Hartmann wavefront sensor, a camera designated for measuring at least one point-spread function of an eccentric wavefront, a circular lenslet array aberrometer, a pyramid wavefront sensor, a phase element based wavefront sensor, a ray tracing aberrometer. However, further kinds of wavefront sensing units may also be feasible.

As generally used, the term "Shack Hartmann wavefront sensor" refers to a particular type of wavefront sensing unit which comprises an array of individual small lenses which are, usually, denoted by the term "lenslets" and a two-dimensional optical detector, such as a CCD array, a CMOS array, or a quad-cell, wherein, upon uniform illumination of the lenslets, an integrated gradient of the incident optical wavefront across each lenslet is proportional to a displacement produced by each individual lenslet. In other words, an aberration of a phase of the incident optical wavefront can, thus, be approximated by a set of local tilts corresponding to the individual lenslets, wherein the tilts corresponding to the lenslets can also denoted by the term "eccentricities." By sampling the incident optical wavefront by virtue of the array of the lenslets in this fashion, the incident optical wavefront can, thus, at least partially, preferably completely, be reconstructed by measuring the local eccentricity of each individual lenslet within the array of the lenslets.

According to the present disclosure, the ocular aberration of the at least one eye of the user is determined from the at least one optical wavefront as measured by the wavefront sensing unit, preferably by the Shack Hartmann wavefront sensor. Herein, the ocular aberration of the at least one eye of the user may, preferably, be determined by measuring at least one of a defocus of the at least one eye or an equivalent sphere across a retinal field of the at least one eye. Preferably, the ocular aberration may be measured in all of at least nine light spots as generated on the surface of the wavefront sensing unit, preferably the Shack Hartmann wavefront sensor, as described below in more detail. As a result, an ocular defocus map which represents the ocular aberration of the retinal field in the at least one eye may, eventually, be obtained. However, it is even more preferred that the ocular defocus map may comprise an interpolation of values which have been generated for the at least nine light spots across the retinal field in the two meridians. As generally used, the term "map" refers to a two-dimensional representation of an object, such that the term "ocular defocus map" relates to a two-dimensional representation of local values of the ocular aberration across the retinal field of the at least one eye of the user, wherein the two axes of the two-dimensional representation are provided by the two meridians.

In particular accordance with the present disclosure, the device for determining at least one ocular aberration of at least one eye of a user comprises at least one diffractive element. As generally used, the term "diffractive element" refers to an optical element designated for diffracting an incident light beam, whereby multiple diffraction orders in the at least one light beam are generated. In particular, the at least one diffractive element may be selected from at least one of an optical grating, a hologram, or a digital light modulation element; however, a further kind of diffractive element may also be feasible. As generally used, the term "optical grating" relates to an optical element having a periodic structure which is designated for splitting and diffracting an incident light beam, whereby multiple diffraction orders in the at least one light beam are generated. As further generally used, the terms "hologram" or "volume hologram" refer to an optical element having an interference pattern being recorded on a physical medium. In particular, the hologram can be computer-generated by modelling and superimposing at least two wavefronts in a digital fashion, whereby a resulting digital image is, subsequently, imprinted onto the physical medium.

As further used herein, the term "digital light modulation element" refers to an optical device having a plurality of individually controllable optical elements designed for modulating an incident light beam. Preferably, the digital light modulation element may be selected from at least one of a spatial light modulator or a digital micro-mirror unit. As generally used, the terms "spatial light modulator" or "SLM" relate to an optical device configured to imprint an intensity pattern on an incident light beam in an electronic and/or an optical fashion. As a result, the spatial light modulator can, typically, be used for generating at least one optical grating. Further, the terms "digital micro-mirror device" or "DMD" refer to an optical device configured to modulate a digital image onto a light beam. For this purpose, the digital micro-mirror device has an arrangement comprising a plurality of tilting micro-mirrors arranged in a matrix, which have an edge length in the micrometer range, each micro-mirror being individually addressable by using electrostatic fields. In this fashion, an incident light beam can be split into individual pixels and, subsequently, be reflected pixel by pixel. However, other types of digital light modulation elements are feasible.

As further generally used, the term "multiple diffraction orders" refers to a kind of splitting of the incident light beam into a plurality of diffracted light beams, wherein each diffracted light beam belongs to a particular diffraction order selected from a single zeroth diffraction order, one of two first diffraction orders, one of two second diffraction orders, or one of higher diffraction orders, wherein a measurable intensity of a particular diffraction order depends on an individual diffraction efficiency of each diffraction order. In practice the multiple diffraction orders of the light beam may, usually, only comprise the zeroth diffraction order and the first diffraction orders, preferably supplemented by the second diffraction orders. However, light beams which may, additionally, comprise the third diffraction orders or the fourth diffraction orders may also be feasible. Thus, in a particularly preferred embodiment, the multiple diffraction orders may at least comprise at least the zeroth diffraction order and the two first diffraction orders in each meridian, whereby at least nine light spots, depending on individual diffraction efficiencies of the multiple diffraction orders, preferably nine to twenty-five light spots, may be generated across the surface of the wavefront sensing unit in the two meridians.

Preferably, the optical grating can be selected from at least one of a transmissive optical grating or a reflective optical grating. Herein, the transmissive optical grating may be advantageous since it allows providing more freedom in placing the optical grating into the at last one optical path. Further, the at least one optical grating can, preferably, be selected from at least one of a diffraction grating or a polarization grating. In contrast to the term "diffraction grating" which refers to the general optical grating as described above, the term "polarization grating" relates to a particular type of optical grating comprising a non-depolarizing polarization element which is designated for altering a polarization state of transmitted light in a periodic fashion, whereby a polarization-dependent diffraction of the transmitted light is obtained. In order to be able to use two consecutive polarization gratings, at least one depolarizer or linear polarizer is placed between the two consecutive polarization gratings.

For the purposes of the present disclosure, the at least one diffractive element is placed in the at least one optical path in a fashion that the desired multiple diffraction orders in the at least one light beam are generated in two meridians in a manner that the multiple diffraction orders are spatially separated as individual light spots in the at least one eye, especially on the retina of the at least one eye of the user and on the surface of the optical wavefront sensing unit. As already defined above, the term "meridian" relates to one of two perpendicular planes of a lens having an astigmatic effect being parallel to the two focal lines. As further generally used, the term "light spot" refers to an impingement of a light beam onto a surface in a manner that a spatially limited area is generated. As a consequence thereof, the multiple diffraction orders of the at least one light beam can be easily distinguished by their position of the corresponding light spot from each other, specifically by the individual lenslets of the Shack Hartmann wavefront sensor. For further details, reference can be made to the description of the exemplary embodiments below.

In order to minimize, preferably to completely avoid, cross talk between the light spots on the surface of the wavefront sensing unit, in particular between the light spots which correspond to individual lenslets in the Shack Hartmann wavefront sensor, it is preferred to adjust parameters of the wavefront sensing unit, in particular of the lenslets in the Shack Hartmann wavefront sensor, accordingly. In general, a high value for a focal length f of the individual lenslet is advantageous for sampling high eccentricities by virtue of Equation (1) which indicates a maximum measurable angle $$\theta_{max} = \frac{\frac{d}{2} - \frac{\rho}{2}}{f}, \quad (1)$$

wherein d is a diameter of the lenslet, ρ is a diameter of a diffraction-limited spot size (Airy disk), and f is the focal length of the lenslet. Herein, exact values for the parameters depend on the Shack Hartmann wavefront sensor itself, the corresponding two-dimensional optical detector, such as the CCD array, the CMOS array, or the quad-cell, and the lenslets. As the Shack Hartmann wavefront sensor may, particularly, be adapted for measuring high values of the eccentricities, a Shack Hartmann wavefront sensor which may exhibit a high dynamic range may be preferred which may, however, result in a lower precision, wherein the lower precision can be offset to a particular extent by choosing a smaller pixel size of the optical detector. For a preferred example of parameters for the Shack Hartmann wavefront sensor, reference can be made to the description of the exemplary embodiments below.

In a particularly preferred embodiment, the at least one diffractive element, in particular the at least one optical grating, which is designated for generating the desired multiple diffraction orders in the at least one light beam in the two meridians may comprise at least one single diffractive element, in particular at least one single optical grating, wherein the at least one diffractive element, in particular the single optical grating, provides a two-dimensional grating which is designated for generating the multiple diffraction orders in the two meridians. For this purpose, the two-dimensional grating of the single diffractive element, in particular the single optical grating, may be provided in form of two individual one-dimensional structures which overlay each other under an angle≠n·180°, wherein n is a natural number including 0, preferably in an orthogonal fashion, whereby a rectangular pattern of beams can be obtained, wherein a diffraction efficiency of the two-dimensional grating equals a product of the two one-dimensional diffraction efficiencies. As used herein, the term "orthogonal" relates to an angle of 90°±45°, preferably of 90°±15°, more preferred of 90°±5°, in particular of 90°±1°, especially of 90°±0.1°. However, further a further angle may also be feasible.

In a preferred alternative embodiment, the at least one diffractive element, in particular the at least one optical grating, which is designated for generating the desired multiple diffraction orders in the at least one light beam in the two meridians may comprise at least two individual diffractive elements, in particular at least two individual optical gratings, wherein each individual diffractive element, in particular each individual optical grating, again, has a one-dimensional grating which is designated for generating the multiple diffraction orders in one meridian, wherein the at least two individual diffractive elements, in particular the at least two individual optical gratings, may be arranged in fashion that the two meridians are arranged orthogonally with respect to each other. With respect to the term "orthogonal," reference can be made to the definition thereof above.

In a further preferred alternative embodiment, the at least one diffractive element, in particular the at least one optical grating, which is designated for generating the desired multiple diffraction orders in the at least one light beam in the two meridians may comprise at least one single diffractive element, in particular at least one single optical grating, wherein the single optical grating, however, provides a one-dimensional grating which is designated for generating the multiple diffraction orders in one meridian, wherein the single optical grating is designated for being rotated in a manner that the multiple diffraction orders are provided in the two meridians. Depending on the type of diffractive element, the single optical grating can be rotated about a rotational axis in a mechanical, an electronic or an optical fashion. For a purpose of mechanically rotating the single optical grating about a rotational axis a known rotating unit can be used.

In a particular embodiment of the present disclosure, the device may comprise at least two diffractive elements, in particular at least two optical gratings, especially at least two two-dimensional gratings or at least three one-dimensional gratings, specifically for generating more than one optical wavefront at the wavefront sensing unit, which can, advantageously, be used for a sampling of values related to the retinal field of the at least one eye of the user.

In a further preferred embodiment of the present disclosure, the at least one diffractive element, in particular the at least one optical grating, may be placed in an entrance pupil plane. As generally used, the term "entrance pupil" refers to an optical image of a physical aperture stop, as viewed through a front of at least one lens, whereas the "entrance pupil plane" relates to a plane perpendicular to an optical axis of the entrance pupil. In this particularly preferred embodiment, the at least one optical element which is designated for guiding the at least one light beam to the at least one eye of the user and to the wavefront sensing unit may, preferably, comprise an optical relay system that may, especially, be designated for relaying the entrance pupil plane onto a pupil of the eye of the user. Herein, the term "optical relay system" refers to a combination of at least two optical elements which is designated for transferring an optical plane to a different opposition. By way of example, information displayed in the entrance pupil plane may, thus, be transferred to be displayed onto the pupil of the eye of the user. Preferably, the relay optical system may comprise a fixed, coaxially mounted pair of wide-angle telecentric lenses, wherein at least one of the lenses can be replaced by a different optical element, such as a spherical mirror. More particular, the optical relay system may comprise an optical relay telescope, also denoted only by the term "telescope" herein, wherein the telescope may have

- at least two individual optical lenses, or at least one assembly comprising at least two individual optical lenses; or
- at least one spherical mirror, and
  - at least one optical lens, or
  - at least one assembly comprising at least two individual optical lenses; or
- at least two spherical mirrors.

As a further alternative, the optical relay system which is designated for relaying the pupil plane to the surface of the wavefront sensing unit may comprise an axicon element which can, preferably, be placed in an intermediate image plane of the telescope. As generally used, the term "axicon element" refers to an optical lens having a conical surface, whereby a light beam, in particular a laser beam, can be transformed into a ring shaped distribution. Consequently, the axicon element laterally shifts the pupils corresponding to the peripheral beams. As a result thereof, at least nine distinct areas are generated on the surface of the wavefront sensing unit, wherein each distinct area comprises one individual light spot which can, thus, be separately processed without having multiple light spots under each lenslet.

In a preferred embodiment, the beam splitter can be placed in a manner that the same optical relay system which is used for relaying the entrance pupil plane onto the pupil of the eye of the user is also designated for relaying the entrance pupil plane to the surface of the wavefront sensing unit, thus, leading to a particularly simple and less expensive device. As used herein, the term "same" refers to a single optical relay system which is designated for being used for at least two different purposes, specifically the two different purposes which are indicated above. Using the same optical relay system for relaying the entrance pupil plane onto the pupil of the eye of the user and for relaying the entrance pupil plane to the surface of the wavefront sensing unit is in particular contrast to US 2005/0105044 A1, which discloses a first optical relay system designated for relaying the entrance pupil plane onto a pupil plane of the at least one eye of the user and a separate second optical relay system designated for relaying the pupil plane of the at least one eye of the user to a surface plane of the wavefront sensing unit. As an alternative, the beam splitter can also be placed close to the eye, for which purpose the device, however, comprises a further optical relay system which is designated for relaying the entrance pupil plane to the surface of the wavefront sensing unit.

In a further preferred embodiment, the device according to the present disclosure may further comprise an additional optical path, wherein a fixation target for the at least one eye of the user may be placed in the additional optical path, wherein the focus of the fixation target may, preferably, be adjusted by using at least one of a tunable lens, a phase modulator, or a Badal lens. As generally used, the term "Badal lens" refers to an optical element comprising at least one lens which is designated for displaying a target under the same angular size. In this further preferred embodiment, the ocular defocus map can be determined during an accommodation phase of the at least one eye of the user. As a result, the determining of the ocular defocus map can, thus, preferably be performed in real-time, which is advantageous compared to X. Wei & L. Thibos, see above, wherein at least one scanning system contributing to a time delay during the measurements is used.

Alternatively or in addition, further embodiments with respect to the device according to the present disclosure are conceivable.

In a further aspect, the present disclosure relates to a method for determining at least one ocular aberration of at least one eye of a user, preferably, by using the device for determining at least one ocular aberration of at least one eye of a user as disclosed elsewhere herein. In particular, the method can be used for individually determining the ocular aberration of both eyes of a user in a consecutive fashion. The method according to the present disclosure comprises the following steps a) and b), which are, preferably, be performed in an order step b) and step a), wherein, these steps can at least partially be performed in a simultaneous manner. In addition, further steps whether disclosed herein or not can, additionally, be performed. The steps of the present method are as follows:

a) measuring at least one optical wavefront comprised by at least one light beam, whereby an ocular aberration of the at least one eye of the user is determined from the at least one optical wavefront; and b) generating multiple diffraction orders in the at least one light beam in two meridians in a manner that the multiple diffraction orders are spatially separated on a wavefront sensing unit and in the at least one eye of the user.

In general, the method according to the present disclosure can be performed in a manual fashion in which a trained eye care professional may perform the indicated steps by using an appropriate device, preferably the device for determining at least one ocular aberration of at least one eye of a user as disclosed elsewhere herein. However, in a preferred embodiment, the method according to the present disclosure may be a computer-implemented method. As generally used, the term "computer-implemented method" refers to a method which involves a programmable apparatus, specifically a computer, a computer network, or a readable medium carrying a computer program, whereby at least one step of the method, in particular step d) is performed by using at least one computer program. For this purpose, the computer program code can be provided on a data storage medium or a separate device such as an optical storage medium, e.g., on a compact disc, directly on a computer or a data processing unit, in particular a mobile communication device, specifically a smartphone or a tablet, or via a network, such as an in-house network or the internet. The present method can, thus, being performed on a programmable unit which is configured for this purpose, such as by providing a particular computer program.

Herein, at least one light beam can be provided along at least one optical path, preferably by using a light source as described above or below in more detail.

Further, the at least one light beam can be guided to the at least one eye of the user and to a wavefront sensing unit. For this purpose, the at least one light beam can, preferably, be split into at least two partial light beams, especially by using a beam splitter as described above or below in more detail, wherein at least one partial light beam is guided to the eye of the user and received from the eye of the user. However, it is actually not a necessity to use a beam splitter as the device according to the present disclosure can function without it. By way of example, the light beam may enter the at least one eye of the user on-axis or at a very small angle with respect to an optical axis, provided that the wavefront sensing unit is not sampling the on-axis aberrations of the eye.

According to step a), at least one optical wavefront comprised by the light beam provided by the eye of the user is measured, preferably by using a wavefront sensing unit, preferably a Shack Hartmann wavefront sensor, as described above or below in more detail, wherein an ocular aberration of the at least one eye of the user is determined from the at least one optical wavefront.

According to step b), multiple diffraction orders in the at least one light beam in two meridians are generated in a manner that the multiple diffraction orders are spatially separated on the wavefront sensing unit, especially on a surface of the wavefront sensing unit, and in the at least one eye of the user. For this purpose, the at least one diffractive element, in particular the at least one optical grating, which is designated for generating the multiple diffraction orders in the at least one light beam in two meridians as described above or below in more detail may, preferably, be used.

In a further aspect, the present disclosure refers to a computer program product which comprises instructions to cause the device for determining at least one ocular aberration of at least one eye of a user according to the present disclosure to execute the steps of the method for determining at least one ocular aberration of at least one eye of a user according to the present disclosure. For this purpose, a computer program may comprise instructions provided by means of a computer program code which are capable of performing any or all of the steps, in particular step a), of the method as described elsewhere herein and, thus, to establish determining the at least one ocular aberration of at least one eye of a user when implemented on a computer or a data processing unit. Herein, the computer program code may be provided on a data storage medium or a separate device such as an optical storage medium, e.g., on a compact disc, directly on a computer or a data processing unit, in particular a mobile communication device, specifically a smartphone or a tablet, or via a network, such as an in-house network or the internet.

In a further aspect, the present disclosure refers to a method for producing at least one spectacle lens for the at least one eye of the user, wherein the producing of the spectacle lens comprises processing a lens blank, wherein the processing of the lens blank is based on instructions configured to compensate at least one ocular aberration of the at least one eye of the user, wherein the determining of the ocular aberration of the at least one eye of the user comprises the steps of the method for determining at least one ocular aberration of at least one eye of a user according to the present disclosure.

For further details concerning the method for determining at least one ocular aberration of at least one eye of a user, the computer program product, or the method for producing at least one spectacle lens for the at least one eye of the user, reference may be made to the device for determining at least one ocular aberration of at least one eye of a user as disclosed elsewhere herein.

When determining the at least one ocular aberration of at least one eye of a user, the device, the computer program product, and the methods according to the present disclosure exhibit various advantages with respect to the prior art. In particular, the device and the method allow generating a whole ocular defocus map of at least one eye of a user in a one-shot assessment by using a simple and easy-to-use approach, in particular without requiring a trained eye care professional, such as an optometrist or an ophthalmologist. Consequently, the device and the method provide a powerful tool for an efficient assessment of a peripheral defocus of the at least one eye of the user, specifically, to obtain a whole ocular defocus map of the at least one eye of the user in a one-shot measurement, especially, by employing an automated measurement of the ocular aberrations with regard to different eccentricities in two meridians which incorporates easy applicability and short test durations. Herein, an implementation of the device as well as an incorporation of the software is designed for making the tool applicable even for untrained users or personnel.

Consequently, the device and the method provide a diagnostic tool for evaluating myopia progression, especially for personalizing myopia control treatments in order to provide personalized optical lenses, such as multifocal contact lenses or progressive spectacles or, especially, myopia progression management (MPM) lenses for peripheral defocus management or defocus incorporated multiple lens segment lenses (DIMS), based on a single and fast measurement of the peripheral defocus of the at least one eye of the user and/or in a continuous monitoring of changes induced by accommodation of the at least one eye of the user or a movement of at least one lens worn by the user.

Summarizing, the exemplary embodiments according to the following clauses are particularly preferred within the scope of the present disclosure:

Clause 1: A device for determining an ocular aberration of at least one eye of a user, the device comprising:
a wavefront sensing unit designated for measuring at least one optical wavefront comprised by at least one light beam, wherein an ocular aberration of the at least one eye of the user is determined from the at least one optical wavefront;
at least one diffractive element designated for generating multiple diffraction orders in the at least one light beam in two meridians in a manner that the multiple diffraction orders are spatially separated on the wavefront sensing unit and in the at least one eye of the user.

Clause 2: The device according to the preceding Clause, wherein the at least one diffractive element is selected from at least one single diffractive element.

Clause 3: The device according to the preceding Clause, wherein the single diffractive element provides a two-dimensional grating designated for generating the multiple diffraction orders in the two meridians.

Clause 4: The device according to any one of the two preceding Clauses, wherein the single diffractive element provides a one-dimensional grating designated for generating the multiple diffraction orders in one meridian.

Clause 5: The device according to the preceding Clause, wherein the single diffractive element is designated for being rotated in a manner that the multiple diffraction orders are provided in the two meridians.

Clause 6: The device according to any one of the preceding Clauses, wherein the at least one diffractive element provides at least two individual optical gratings.

Clause 7: The device according to the preceding Clause, wherein each individual optical grating provides a one-dimensional grating designated for generating the multiple diffraction orders in one meridian.

Clause 8: The device according to the preceding Clause, wherein the two meridians are arranged orthogonally with respect to each other.

Clause 9: The device according to the preceding Clause, wherein the term "orthogonal" relates to an angle of 90°±45°, preferably of 90°±15°, more preferred of 90°±5°, in particular of 90°±1°, especially of 90°±0.1°.

Clause 10: The device according to any one of the preceding Clauses, comprising at least two diffractive elements, wherein the at least two diffractive elements are designated for generating more than one optical wavefront in the eye of the user and on the wavefront sensing unit.

Clause 11: The device according to the preceding Clause, wherein the at least one diffractive element is selected from at least one of an optical grating, a hologram, or a digital light modulation element.

Clause 12: The device according to the preceding Clause, wherein the at least one optical grating is selected from at least one of a diffraction grating or a polarization grating.

Clause 13: The device according to the preceding Clause, wherein at least one depolarizer or linear polarizer is placed between two polarization gratings.

Clause 14: The device according to any one of the three preceding Clauses, wherein the at least one optical grating is selected from at least one of a transmissive optical grating or a reflective optical grating.

Clause 15: The device according to any one of the four preceding Clauses, wherein the at least one hologram is a volume hologram.

Clause 16: The device according to any one of the five preceding Clauses, wherein the at least one the digital light modulation element is selected from at least one of a spatial light modulator or a digital micro-mirror unit.

Clause 17: The device according to any one of the preceding Clauses, further comprising at least one optical element designated for guiding the at least one light beam to the at least one eye of the user and to the wavefront sensing unit.

Clause 18: The device according to the preceding Clause, wherein the at least one optical element comprises a beam splitter designated for splitting the at least one light beam into at least two partial light beams, wherein at least one of the partial light beams is guided to the at least one eye of the user.

Clause 19: The device according to any one of the two preceding Clauses, wherein the at least one diffractive element is placed in an entrance pupil plane.

Clause 20: The device according to the preceding Clause, wherein the at least one optical element comprises an optical relay system designated for relaying the entrance pupil plane onto a pupil plane of the at least one eye of the user.

Clause 21: The device according to the preceding Clause, wherein the optical relay system comprises at least one of: a telescope having at least two individual optical lenses or at least one assembly comprising at least two individual optical lenses, or having at least one spherical mirror and at least one optical lens or at least one assembly comprising at least two individual optical lenses, or having at least two spherical mirrors.

Clause 22: The device according to the preceding Clause, further comprising an axicon element designated for relaying the pupil plane of the at least one eye of the user to the wavefront sensing unit.

Clause 23: The device according to the preceding Clause, wherein the axicon element is, preferably, placed in an intermediate image plane of the telescope.

Clause 24: The device according to any one of the three preceding Clauses, wherein the beam splitter is placed in a manner that the same optical relay system is designated for relaying the entrance pupil plane to a surface of the wavefront sensing unit.

Clause 25: The device according to any one of the four preceding Clauses, wherein the beam splitter is placed close to the at least one eye of the user, wherein the device comprises a further optical relay system designated for relaying the entrance pupil plane to a surface of the wavefront sensing unit.

Clause 26: The device according to any one of the preceding Clauses, wherein the wavefront sensing unit is selected from at least one of: a Shack Hartmann wavefront sensor, a camera designated for measuring at least one point-spread function of an eccentric wavefront, a circular lenslet array aberrometer, a pyramid wavefront sensor, a phase element based wavefront sensor, a ray tracing aberrometer.

Clause 27: The device according to any one of the preceding Clauses, further comprising a light source designated for providing at least one light beam.

Clause 28: The device according to the preceding Clause, wherein the light source is or comprises a monochromatic light source, or a combination of polychromatic source and a tunable or fixed bandwidth filter, or a combination of a supercontinuum source and a tunable or fixed bandwidth filter.

Clause 29: The device according to any one of the preceding Clauses, wherein the monochromatic light source is or comprises a laser diode.

Clause 30: The device according to any one of the preceding Clauses, further comprising at least one additional optical path, wherein at least one of a fixation target and a pupil camera are placed in the additional optical path.

Clause 31: The device according to the preceding Clause, wherein the focus of the fixation target is adjusted by using at least one of: a tunable lens, phase modulator, or a Badal lens.

Clause 32: A method for determining an ocular aberration of at least one eye of a user, the method comprising the following steps:
  a) measuring at least one optical wavefront comprised by the at least one light beam, whereby an ocular aberration of the at least one eye of the user is determined from the at least one optical wavefront;
  b) generating multiple diffraction orders in the at least one light beam in two meridians in a manner that the multiple diffraction orders are spatially separated on a wavefront sensing unit and in the at least one eye of the user.

Clause 33: The method according to the preceding Clause, wherein a single diffractive element providing a two-dimensional grating is generating the multiple diffraction orders in the two meridians.

Clause 34: The method according to any one of the preceding Clauses referring to a method, wherein at least one single diffractive element providing a one-dimensional grating is generating the multiple diffraction orders in one meridian, and is being rotated in a manner that the multiple diffraction orders are provided in the two meridians.

Clause 35: The method according to any one of the preceding Clauses referring to a method, wherein at least two individual optical diffractive elements are generating the multiple diffraction orders in one meridian, wherein the at least two meridians are arranged orthogonally with respect to each other.

Clause 36: The method according to the preceding Clause, wherein the term "orthogonal" relates to an angle of 90°±45°, preferably of 90°±15°, more preferred of 90°±5°, in particular of 90°±1°, especially of 90°±0.1°.

Clause 37: The method according to any one of the preceding Clauses referring to a method, wherein the at least two diffractive elements are generating more than one optical wavefront.

Clause 38: The method according to any one of the preceding Clauses referring to a method, wherein the ocular aberration of the at least one eye of the user is determined by measuring at least one of a defocus of the at least one eye of the user or an equivalent sphere across a retinal field of the at least one eye of the user, whereby an ocular defocus map representing the ocular aberration of the retinal field in the at least one eye of the user is obtained.

Clause 39: The method according to any one of the preceding Clauses referring to a method, wherein the multiple diffraction orders comprise at least a zeroth diffraction order and at least two first diffraction orders in each meridian, whereby at least nine light spots are generated across the wavefront sensing unit in the two meridians.

Clause 40: The method according to the preceding Clause, whereby, depending on individual diffraction efficiencies of the multiple diffraction orders, nine to twenty-five light spots are generated across the wavefront sensing unit in the two meridians.

Clause 41: The method according to any one of the three preceding Clauses, wherein the ocular defocus map comprises at least one of: values related to the at least nine light spots generated across the wavefront sensing unit in the two meridians, or values interpolated between the at least nine light spots generated across the wavefront sensing unit Clause 42: The method according to any one of the preceding Clauses referring to a method, further comprising the step of:

guiding the at least one light beam to the at least one eye of the user and to the wavefront sensing unit.

Clause 43: The method according to any one of the preceding Clauses referring to a method, further comprising the step of:

providing at least one light beam along at least one optical path.

Clause 44: The method according to any one of the preceding Clauses referring to a method, further comprising an additional optical path, wherein at least one of a fixation target and a pupil camera are placed in the additional optical path.

Clause 45: The method according to the preceding Clause, wherein the focus of the fixation target is adjusted by using at least one of: a tunable lens, phase modulator, or a Badal lens.

Clause 46: The method according to any one of the two preceding Clauses, wherein the ocular defocus map is measured during an accommodation of the at least one eye of the user.

Clause 47: The method according to the preceding Clause, wherein the ocular defocus map is measured in real-time.

Clause 48: A computer program product comprising instructions to cause the device according to any one of the preceding Clauses referring to a device to execute the steps of the method for determining an ocular aberration of at least one eye of a user in at least two meridians according to any one of the preceding Clauses referring to a method.

Clause 49: A method for producing at least one spectacle lens for the at least one eye of the user, wherein the producing of the spectacle lens comprises processing a lens blank, wherein the processing of the lens blank is based on instructions configured to compensate at least one ocular aberration of the at least one eye of the user, wherein a method for determining of the ocular aberration of the at least one eye of the user comprises the steps of the method according to any one of the preceding Clauses referring to a method for determining an ocular aberration of at least one eye of a user.

Further optional features and exemplary embodiments of the present disclosure are disclosed in more detail in the subsequent description of preferred embodiments, preferably in conjunction with the dependent claims. Therein, the respective optional features may be implemented in an isolated fashion as well as in any arbitrary feasible combination, as the skilled person will realize. It is emphasized here that the scope of the disclosure is not restricted by the exemplary embodiments.

BRIEF DESCRIPTION OF THE DRAWINGS

The disclosure will now be described with reference to the drawings wherein.

DESCRIPTION OF EXEMPLARY EMBODIMENTS

Figure 1:
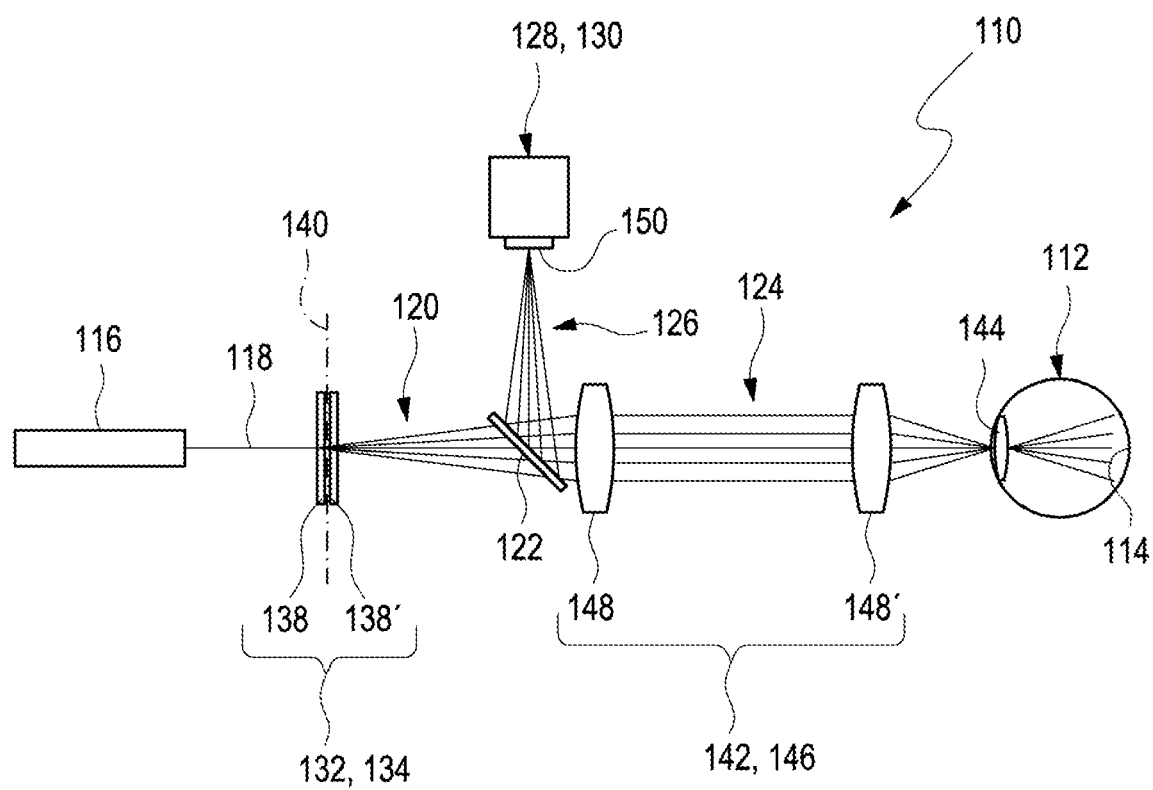
FIG. 1 illustrates a preferred embodiment of a device for determining at least one ocular aberration of at least one eye of a user according to the present disclosure.

FIG. 1 illustrates a preferred embodiment of a device 110 for determining at least one ocular aberration of at least one eye 112 of a user, wherein the eye 112 comprises a retina 114. In the following, the FIGS. and the description refer, for sake of simplicity, however, only to one eye 112 of the user. As schematically depicted there, the device 110 may comprise a light source 116, preferably a monochromatic source, most preferred a laser diode, particularly by virtue of its simplicity, easy availability and considerably low expenses. However, as already indicated above, a different type of light source may also be feasible. Herein, the light comprises electromagnetic radiation preferably in at least one of the visible spectral range or the near infrared spectral range, thus, having a wavelength of 380 nm to 1.5 µm. Accordingly, the light source 116 is designated for generating a light beam 118, which is guided along an optical path 120. Herein, the light beam 118 describes a propagation of the light in form of rays, wherein a direction of propagation of the rays is, generally, denoted as the optical path 120. Further, a surface being perpendicular to the direction of propagation of the rays is denoted as optical wavefront (not depicted here).

As further illustrated in FIG. 1, the device 110 may further comprise a beam splitter 122, which can be selected from any known beam splitter, in particular from a glass plate with dielectric coating, a dichroic mirror, a pellicle beam splitter, a beam splitter plate, or a polarizing beam splitter, such as a Wollaston prism, or a polarization grating. However, a different type of beam splitter may also be feasible. As schematically depicted in FIG. 1, the beam splitter 122 can, preferably, be placed in the optical path 120 in a fashion that it may split the light beam 118 as provided by the light source 116 into two partial light beams 124, 126. As a result thereof, a first partial light beam 124 is guided to the eye 112 of the user and, after being reflected by the eye 112 of the user received from the eye 112 of the user, especially for being guided via a second partial light beam 126 towards a wavefront sensing unit 128. However, as explained above in more detail, the device 110 may comprise further embodiments which are devoid of the beam splitter 122.

Figure 6:
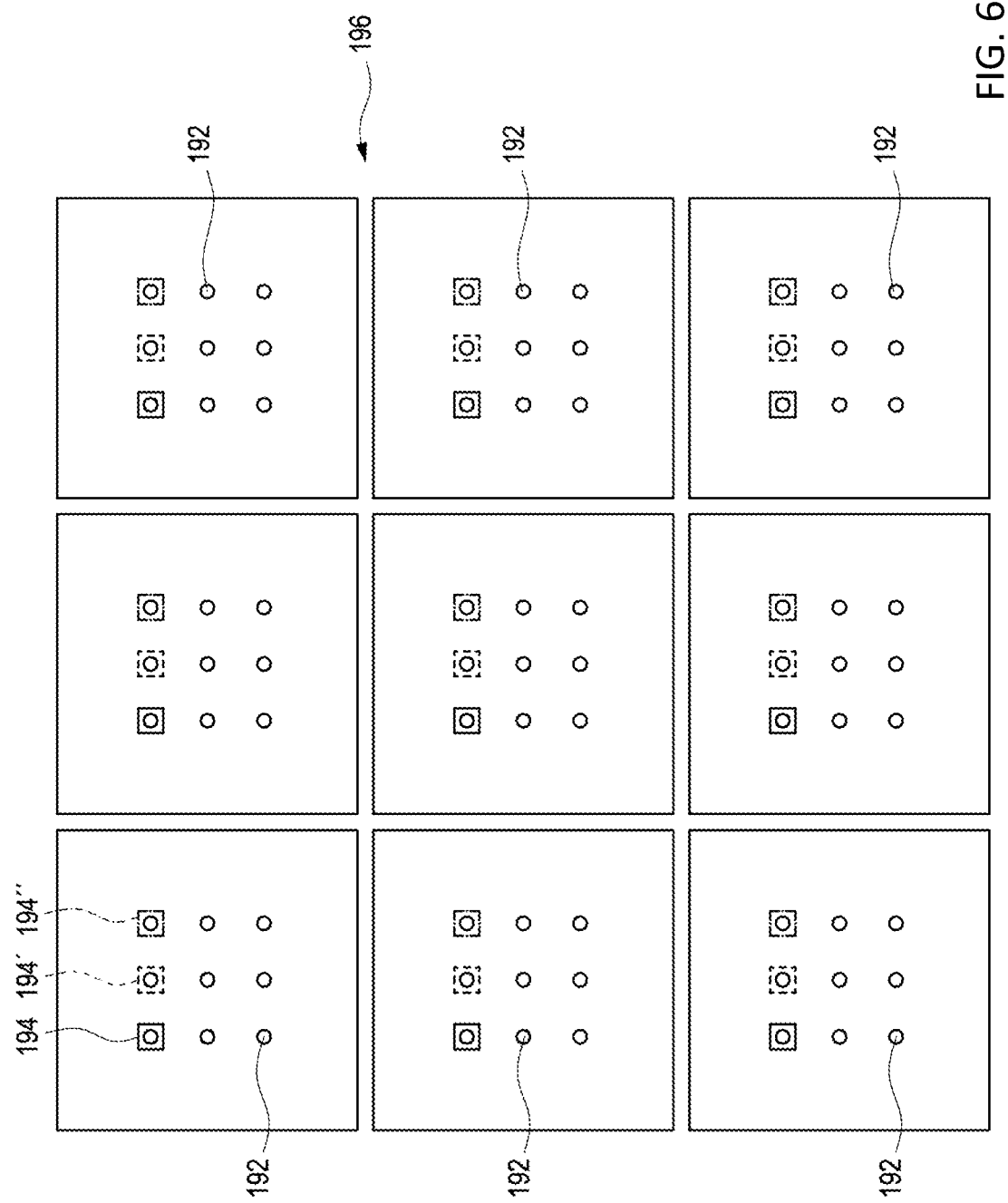
FIG. 6 illustrates a diagram indicating a spatial separation of multiple diffraction orders on the Shack Hartmann wavefront sensor.

As further illustrated in FIG. 1, the device 110 further comprises the wavefront sensing unit 128, in particular a Shack Hartmann wavefront sensor 130. However, a further kind of wavefront sensing unit, in particular a camera designated for measuring at least one point-spread function of an eccentric wavefront, a circular lenslet array aberrometer, a pyramid wavefront sensor, a phase element based wavefront sensor, or a ray tracing aberrometer, may also be feasible. Herein, the wavefront sensing unit 128, in particular the Shack Hartmann wavefront sensor 130, is designated for measuring aberrations of the optical wavefront without requiring interference with a reference beam having no aberrations. In particular, the Shack Hartmann wavefront sensor 130 has an array of individual lenslets (not depicted here) a two-dimensional optical detector, such as a CCD array, a CMOS array, or a quad-cell as depicted in FIG. 6. Accordingly, the ocular aberration of the eye 112 of the user is determined from the optical wavefront measured by the wavefront sensing unit 128, in particular the Shack Hartmann wavefront sensor 130.

As further illustrated in FIG. 1, the device 110 further comprises a diffractive element. In the exemplary embodiments used herein, the diffractive element is an optical grating 132; however, using, alternatively or in addition, a hologram, such as a volume hologram, and/or a digital light modulation element, such as a spatial light modulator (SLM) or a digital micro-mirror unit (DMD) may also be feasible for the purposes of the present disclosure.

Figure 2:
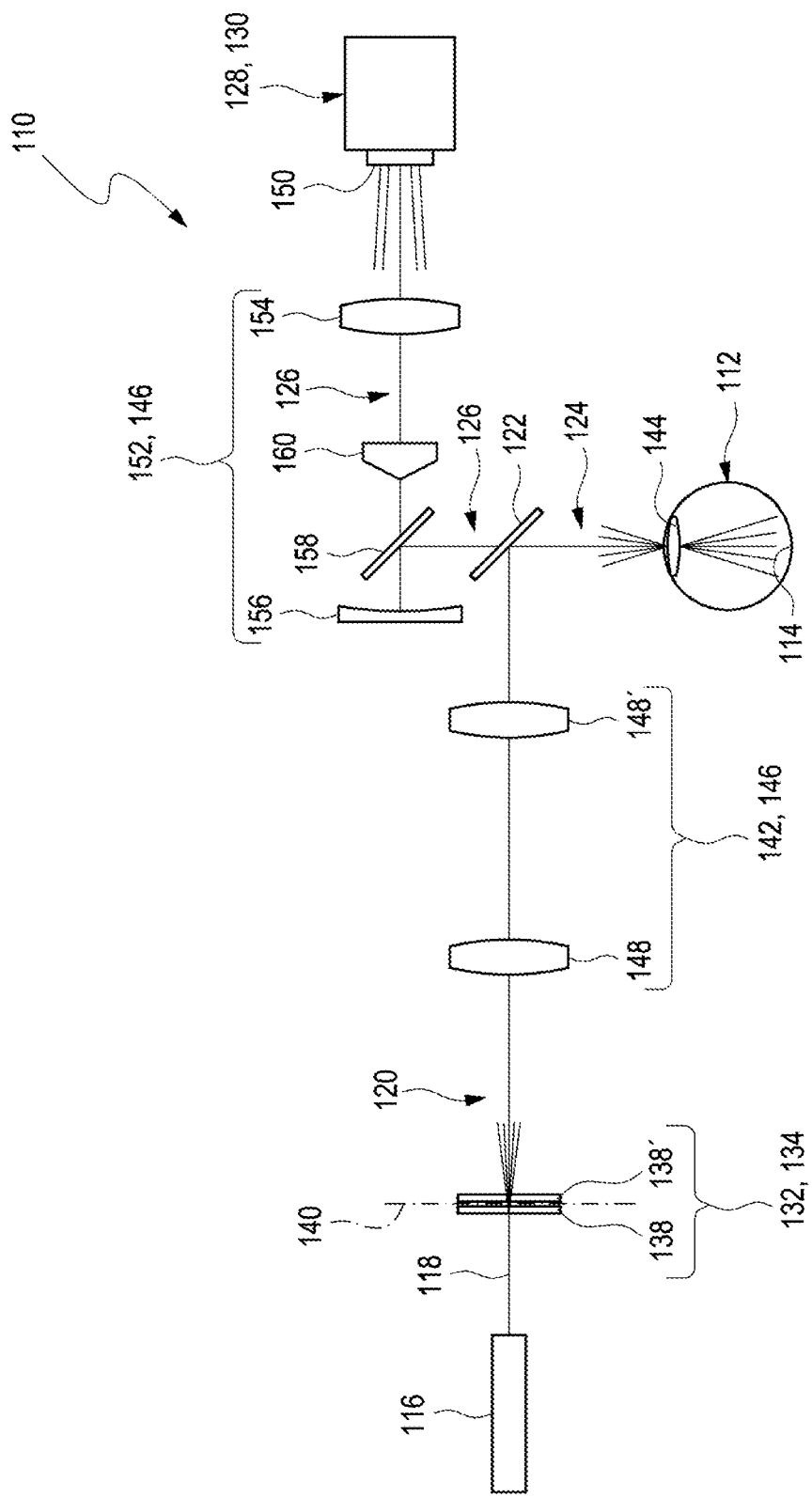
FIG. 2 illustrates a further preferred embodiment of the device for determining the at least one ocular aberration of the at least one eye of the user according to the present disclosure.
Figure 3:
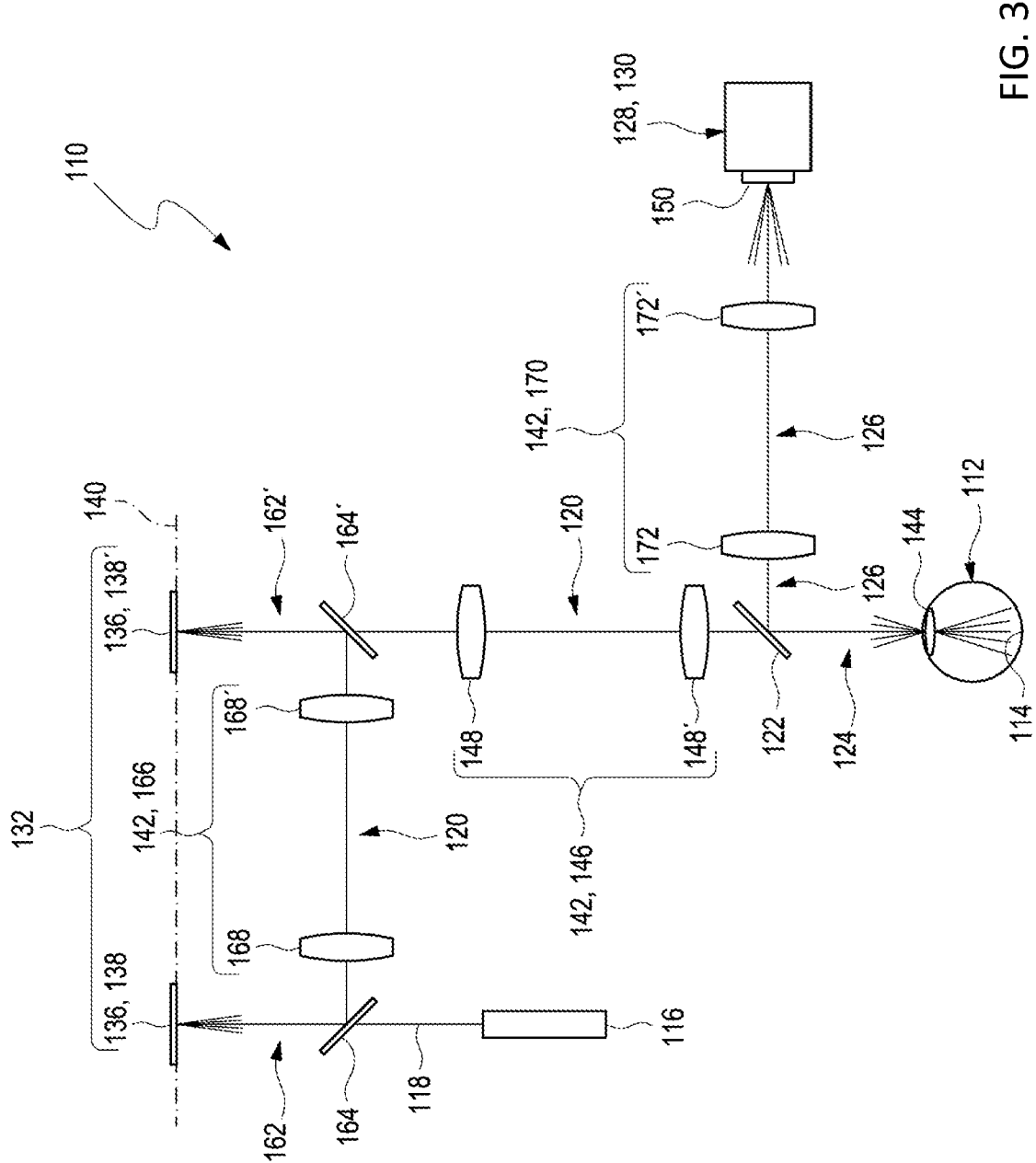
FIG. 3 illustrates a further preferred embodiment of the device for determining the at least one ocular aberration of the at least one eye of the user according to the present disclosure.
Figure 4:
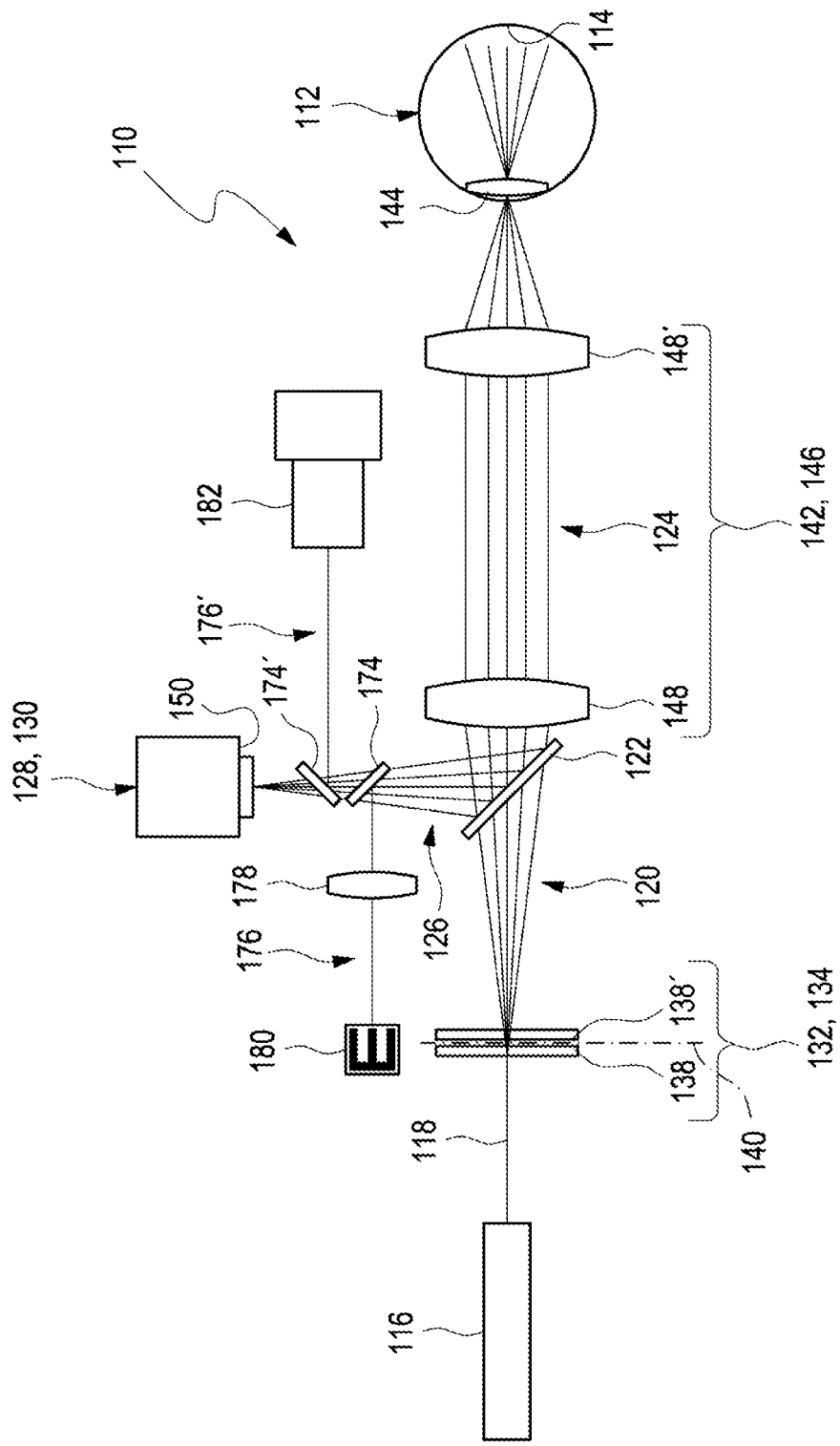
FIG. 4 illustrates a further preferred embodiment of the device for determining the at least one ocular aberration of the at least one eye of the user according to the present disclosure.
Figure 5:
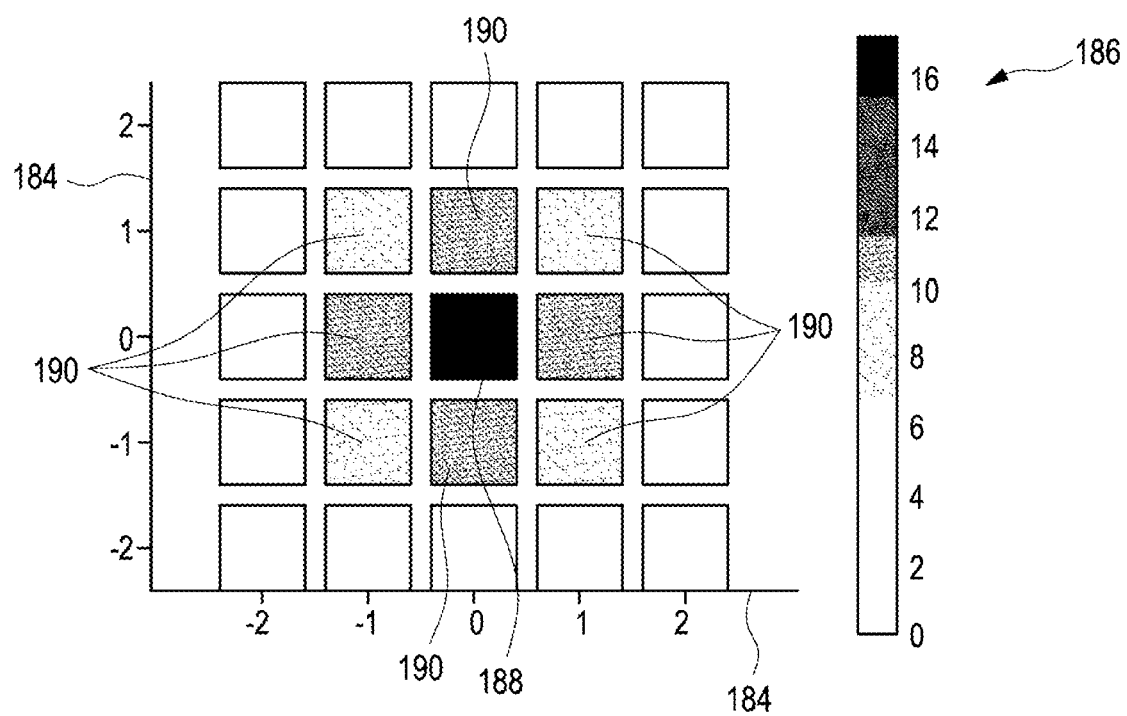
FIG. 5 illustrates a diagram indicating an energy spread across different diffraction orders.

In the exemplary embodiments of FIGS. 1, 2, and 4, the optical grating is a transmissive optical grating 134, thus allowing the light beam 118 to traverse the optical grating 132. However, as schematically depicted in FIG. 3, a reflective optical grating 136 may also be feasible. As described above, the optical grating 132 can, further, be selected from a diffraction grating or a polarization grating. As a result of traversing the transmissive optical grating 134 or, alternatively, being reflected by the reflective optical grating 136, multiple diffraction orders as schematically depicted in FIGS. 5 and 6 are generated in the light beam 118. Herein, the optical grating 132 is placed in the at least one optical path 118 in a fashion that the desired multiple diffraction orders in the light beam 118 are generated in two meridians in a manner that the multiple diffraction orders are spatially separated as individual light spots in the eye 112, especially on the retina 114, of the user and on the optical wavefront sensing unit as further illustrated in FIGS. 5 and 6.

As further illustrated in FIG. 1, the optical grating 132 which is designated for generating the desired multiple diffraction orders in the at least one light beam 118 in the two meridians comprises two individual optical gratings 138, 138' each having a one-dimensional grating designated for generating the multiple diffraction orders in one meridian, wherein the two individual optical gratings 138, 138' are arranged orthogonally with respect to each other in order to generate the desired multiple diffraction orders in the at least one light beam 118 in the two meridians. With respect to the term "orthogonal," reference can be made to the definition thereof above. As an alternative, a single optical grating (not depicted here) could also be used, wherein the single optical grating having a one-dimensional grating designated for generating the multiple diffraction orders in one meridian can be rotated in a fashion that the multiple diffraction orders are provided in the two meridians. As a further alternative, the single optical grating can be two-dimensional which is designated for generating the multiple diffraction orders in the two meridians. As schematically depicted in FIG. 1, the optical grating 132 may, preferably, be placed in an entrance pupil plane 140.

As further illustrated in FIG. 1, the device 110 may further comprise at least one optical element which is designated for guiding the at least one light beam 118 to the at least one eye 112 of the user and to a wavefront sensing unit 128. For this purpose, the at least one optical element may, preferably, comprise an optical relay system 142 which is, especially, be designated for relaying the entrance pupil plane 140 onto a pupil 144 of the eye 112 of the user, and, in addition, the beam splitter 122 which is, as described above in more detail, designated for guiding the light beam 118, in particular the partial light beam 126, on the wavefront sensing unit 128.

As schematically depicted in FIG. 1, the optical relay system 142 may, preferably, comprise a telescope 146 having two wide-angle telecentric lenses 148, 148', which are shown in FIG. 1 as single lenses for simplification purposes and which are designated for transferring information displayed in the entrance pupil plane 140 to be displayed onto the pupil 144 of the eye 142 of the user. For a further kind of optical relay system reference may be made to FIG. 2 as well as to the description above.

As further illustrated in FIG. 1, the beam splitter 122 can be placed in a manner that the same optical relay system 142 which is used for relaying the entrance pupil plane 140 onto the pupil 144 of the eye 112 of the user is also designated for relaying the entrance pupil plane 140 to a surface 150 of the wavefront sensing unit 128, whereby a particularly simple and less expensive device 110 can be obtained. An alternative embodiment thereof is schematically depicted in FIG. 3.

FIG. 2 illustrates a further preferred embodiment of the device 110 for determining the at least one ocular aberration of the eye 112 of the user. The particular embodiment of the device 110 as schematically depicted there, differs from the particular embodiment of the device 110 as displayed in FIG. 1, that, in addition to the telescope 146 which constitutes the optical relay system 142 comprises a further telescope 152, which in addition to a further wide-angle telecentric lens 154, has a spherical mirror 156, a further beam splitter 158, and an axicon element 160 which is placed in an intermediate image plane of the further telescope 152. As described above, the axicon element 160 has a conical surface, hereby transforming the light beam 118 into a ring shaped distribution. As a result thereof, the axicon element 160 laterally shifts the pupils corresponding to the peripheral beams. As schematically depicted in FIGS. 5 and 6, the axicon element 160 generated distinct areas on the surface 150 of the wavefront sensing unit 128, wherein each distinct area comprises one individual light spot which can, thus, be separately processed without having multiple light spots under each lenslet.

For further details concerning FIG. 2, reference can be made to the exemplary embodiment of the device 110 as described above with respect to FIG. 1.

FIG. 3 illustrates a further preferred embodiment of the device 110 for determining the at least one ocular aberration of the eye 112 of the user. The particular embodiment of the device 110 as schematically depicted there, differs from the particular embodiment of the device 110 as displayed in FIG. 1, in that each of the two individual optical gratings 138, 138' which has a one-dimensional grating designated for generating the multiple diffraction orders in one meridian is each a reflective optical grating 136 which is placed in an individual additional optical path 162, 162', thus, requiring two additional beam splitters 164, 164'. Herein, the first individual optical grating 138 may, preferably, be placed in the entrance pupil plane 140 as described above with respect to FIG. 1. Multiple diffraction orders in one meridian are then reflected from the first individual optical grating 138. A further telescope 166 comprising further wide-angle telecentric lenses 168, 168' relays here the entrance pupil plane 140 onto the second individual optical grating 138' being oriented orthogonally with respect to the first individual optical grating 138. In reflection, each light beam 118 as provided by the first individual optical grating 138 is separated again, resulting in multiple diffraction orders in the two meridians.

As further illustrated in FIG. 3, the beam splitter 122 can also be placed close to the eye 112 of the user. In this arrangement, however, the device 110 further comprises a further telescope 170 having further wide-angle telecentric lenses 172, 172', wherein the further telescope 170 is designated for relaying the entrance pupil plane 140 to the surface 150 of the wavefront sensing unit 128. Herein, the further telescope 170 comprising the further wide-angle telecentric wide-angle telecentric lenses 172, 172' then relays the entrance pupil plane 140 to the pupil 144 of the eye 112 of the user, where all incident light multiple diffraction orders of the light beam 118 converge in a singular spot. As a result, point sources across the retina 114 of the eye 112 of the user are generated. The telescope 146 comprising the wide-angle telecentric lenses 148, 148' conjugates the entrance pupil plane 140 to the surface 150 of the wavefront sensing unit 128, wherein the optical wavefronts resulting from each eccentricity are sampled.

For further details concerning FIG. 3, reference can be made to the exemplary embodiment of the device 110 as described above with respect to FIG. 1.

FIG. 4 illustrates a further preferred embodiment of the device 110 for determining the at least one ocular aberration of the eye 112 of the user. In this particular embodiment, the ocular defocus map can be determined from the optical wavefront even during an accommodation of the eye 112 of the user. As schematically depicted in FIG. 4, the device 110 further comprises, for this purpose, additional beam splitters 174, 174' which open additional optical paths 176, 176'. As an alternative, the device 110 may further comprise dichroic mirrors (not depicted here), wherein the dichroic mirrors are long-pass mirrors, thus, being designated for reflecting shorter wavelengths. In particular, one of the dichroic mirrors is designated to reflect a shortest portion of the wavelengths while a further of the dichroic mirrors is designated to reflect a middle portion of the wavelengths. As a result, the longest portion of the wavelengths can pass to the wavefront sensing unit 128.

In the exemplary embodiment of FIG. 4, the first additional optical path 176 comprises a tunable lens 178 for adjusting the focus of a fixation target 180, wherein the tunable lens 178 can be replaced by a phase modulator or a Badal lens. Further, the second additional optical path 176' comprises a pupil camera 182 which is designated for, simultaneously, measuring a movement of the pupil 144 of the eye 112 of the user and controlling a position of the pupil 144 of the eye 112 of the user to the fixation target 180 during accommodation. As a result thereof, the at least one ocular aberration of the eye 112 of the user can be determined in this fashion as a function of the accommodation of the at least one eye 112 of the user.

For further details concerning FIG. 4, reference can be made to the exemplary embodiment of the device 110 as described above with respect to FIG. 1.

FIG. 5 illustrates a diagram indicating an energy spread across the multiple diffraction orders 184, wherein a phase modulation depth of the sinusoidal diffraction grating 132 assumes a values of 0.4 π. As described above, the diffraction order 184 can be selected from a single zeroth diffraction order, one of two first diffraction orders, one of two second diffraction orders, or one of higher diffraction orders, wherein a measurable intensity of the diffraction order 184 depends on an individual diffraction efficiency 186 of each diffraction order 184. The diagram as schematically depicted in FIG. 5, allows performing a single foveal measurement 188 and at eight peripheral measurements 190 when taking into account the first diffraction orders, or twenty-five peripheral measurements 190 when, additionally, taking into account the second diffraction orders. Herein, an increase of the value of the phase modulation depth, typically, results in energy balance shifting to higher diffraction orders. If the optical grating 132 is a sinusoidal optical grating, the diffraction efficiency 186 of the multiple diffraction orders 184 can be described by using Bessel functions related to the corresponding multiple diffraction orders 184.

FIG. 6 illustrates a diagram indicating a spatial separation of the multiple diffraction orders 184 on the Shack Hartmann wavefront sensor 130. When the multiple diffraction orders 184 within the light beam 118 are combined at the entrance pupil plane 140, each lenslet of the Shack Hartmann wavefront sensor 130 can produce multiple light spots 192 as schematically depicted in FIG. 6. Herein, pitch and focal length of the lenslets are, preferably, selected in order to minimize, preferably to completely avoid, cross talk between the multiple light spots 192 on the surface 150 of the Shack Hartmann wavefront sensor 130. In FIG. 6, light spots 194, 194', 194" which correspond to the same diffraction order 184, are separated from the other diffraction orders 184 and processed individually. Further, a grid 196 as depicted there separates areas of the Shack Hartmann wavefront sensor 130 under each lenslet.

Based on Equation 1 above, a preferred example of parameters for the Shack Hartmann wavefront sensor 130 can be estimated. Using an optical relay having a magnification of 2.5 from the surface 150 of the Shack Hartmann wavefront sensor 130 to entrance pupil plane 140, two meridians covering a field of ±20° at the entrance pupil plane 140 and ±8° at the surface 150 of the Shack Hartmann wavefront sensor 130 are obtained. Taking into account a lenslet pitch of 1 mm;
    a lenslet focal length of 3 mm; and
    a wavelength of the light of 850 nm which is used for an Airy disk calculation), the Shack Hartmann wavefront sensor 130 could be able to measure a maximum angle of 9.53°. The eccentric beams correspond to a tilt of 8°. The dynamic range of the Shack Hartmann wavefront sensor 130 could, thus correspond, to a maximum wavefront tilt of 1.53°. By selecting these parameters no cross talk between the sensor areas under the lenslets may occur.

In addition, the dynamic range of the Shack Hartmann wavefront sensor 130 sensor can be improved by using advanced processing methods, as e.g., described by Lundström, L., & Unsbo, P. (2004), *Unwrapping Hartmann-Shack images from highly aberrated eyes using an iterative B-spline based extrapolation method*, Optometry and Vision Science, 81(5), 383-388.

Figure 7:
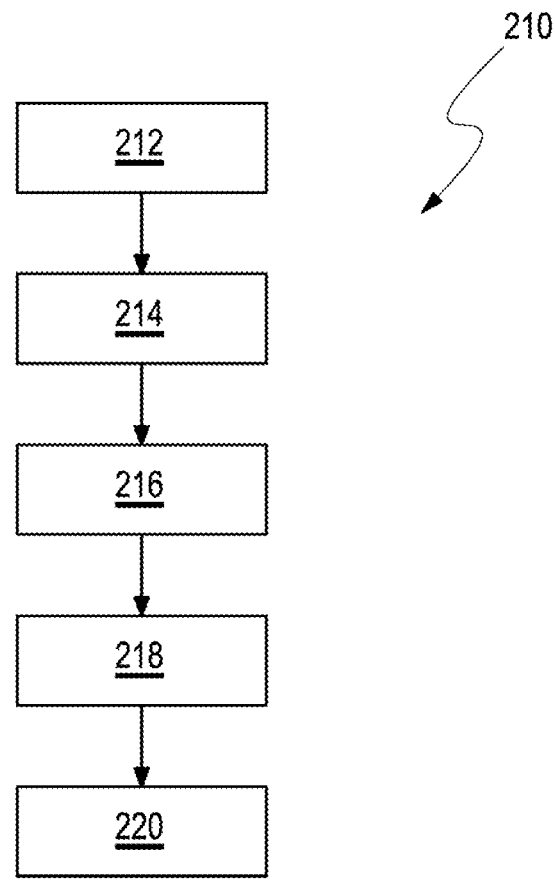
FIG. 7 illustrates a preferred embodiment of a method for determining at least one ocular aberration of at least one eye of a user according to the present disclosure.

FIG. 7 schematically illustrates a preferred embodiment of a method 210 for determining the at least one ocular aberration of the at least one eye 112 of the user according to the present disclosure.

In an illuminating step 212, the light beam 118 along the optical path 120 can be provided, preferably by using the light source 116, in particular the laser diode.

In a diffracting step 214 according to step b), the multiple diffraction orders 168 are generated in the light beam 118 in two meridians in a manner that the multiple diffraction 168 orders are spatially separated in the eye 112, especially on the retina 114, of the user and on the wavefront sensing unit 128.

In a guiding step 216, the light beam 118 which comprises the multiple diffraction orders 168 can be guided to the at least one eye 112 of the user and to the wavefront sensing unit 128. For this purpose, the light beam 118 may be split into the two partial light beams 124, 126, wherein the first partial light beam 124 may be guided to the eye 112, especially to the retina 114, of the user and received from the eye 112 of the user, especially for being guided via the second partial light beam 126 towards the wavefront sensing unit 128, especially to the surface 150 of the Shack Hartmann wavefront sensor 130.

In a measuring step 218 according to step a), the optical wavefront comprised by the light beam 118, especially by the second partial light beam 126, is measured, preferably in real-time, whereby an ocular defocus map 220 representing the ocular aberration of the retinal field in the eye 112 of the user is determined from the optical wavefront, preferably in a one-shot measurement of the eye 112 of the user. Herein, the ocular defocus map 220 may, preferably, comprise the values related to the multiple light spots 176 as generated across the wavefront sensing unit 128 in the two meridians or, more preferred, values interpolated between the multiple light spots 176. In addition, at least one algorithm, preferably selected from machine learning, or artificial intelligence, can be used for further improving the measurements.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

LIST OF REFERENCE SIGNS

110 device for determining at least one ocular aberration of at least one eye of a user
112 eye
114 retina
116 light source
118 light beam
120 optical path
122 beam splitter
124 first partial light beam
126 second partial light beam
128 wavefront sensing unit
130 Shack Hartmann wavefront sensor
132 optical grating
134 transmissive optical grating
136 reflective optical grating
138, 138' individual optical grating
140 entrance pupil plane
142 optical relay system
144 pupil
146 telescope
148, 148' wide-angle telecentric lens
150 surface
152 further telescope
154 further wide-angle telecentric lens
156 spherical mirror
158 further beam splitter
160 axicon element
162, 162' additional optical path
164, 164' additional beam splitter
166 further telescope
168, 168' further wide-angle telecentric lens
170 further telescope
170, 172' further wide-angle telecentric lens
174, 174' additional beam splitter
176, 176' additional optical path
178 tunable lens
180 focus-adjustable fixation target
182 pupil camera
184 diffraction order
186 diffraction efficiency
188 foveal measurement
190 peripheral measurement
192 light spot
194, 194' light spot
196 grid
210 method
212 illuminating step
214 diffracting step
216 guiding step
218 measuring step
220 ocular defocus map

The invention claimed is:

1. A method for determining an ocular aberration of at least one eye of a user, the method comprising the following steps:
   a) measuring at least one optical wavefront comprised by at least one light beam, wherein an ocular aberration of the at least one eye of the user is determined from the at least one optical wavefront; and
   b) generating multiple diffraction orders in the at least one light beam in two meridians in a manner that the multiple diffraction orders are spatially separated in the at least one eye of the user and on the wavefront sensing unit,
   wherein
the multiple diffraction orders include at least a zeroth diffraction order and at least two first diffraction orders in each meridian, wherein at least nine light spots are generated across the wavefront sensing unit in the two meridians.

2. The method according to claim 1, wherein
   a single diffractive element providing a two-dimensional grating is generating the multiple diffraction orders in the two meridians; or
   at least two individual diffractive elements are generating the multiple diffraction orders in one meridian, wherein the at least two individual meridians are arranged orthogonally with respect to each other; or
   at least one single diffractive element providing a one-dimensional grating is generating the multiple diffraction orders in one meridian, and is being rotated in a manner that the multiple diffraction orders are provided in the two meridians.

3. The method according to claim 1, wherein the ocular aberration of the at least one eye of the user is determined by measuring at least one of a defocus of the at least one eye of the user, or an equivalent sphere across a retinal field of the at least one eye of the user, and wherein an ocular defocus map representing the ocular aberration of the retinal field in the at least one eye of the user is obtained.

4. The method according to claim 3, wherein the ocular defocus map comprises values related to the at least nine light spots generated across the wavefront sensing unit in the two meridians or values interpolated between the at least nine light spots generated across the wavefront sensing unit.

5. The method according to claim 1, wherein at least one of a focus-adjustable fixation target and a pupil camera are placed in at least one additional optical path, and wherein the ocular defocus map is measured during an accommodation of the at least one eye of the user to the fixation target.

6. A method for producing at least one spectacle lens for the at least one eye of the user, wherein the producing of the spectacle lens comprises processing a lens blank, wherein the processing of the lens blank is based on instructions configured to compensate at least one ocular aberration of the at least one eye of the user, and wherein the ocular aberration of the at least one eye is determined by a method for determining an ocular aberration of at least one eye of a user, the method comprising the following steps:
   a) measuring at least one optical wavefront comprised by at least one light beam, wherein an ocular aberration of the at least one eye of the user is determined from the at least one optical wavefront; and
   b) generating multiple diffraction orders in the at least one light beam in two meridians in a manner that the multiple diffraction orders are spatially separated in the at least one eye of the user and on the wavefront sensing unit,
   wherein the multiple diffraction orders include at least a zeroth diffraction order and at least two first diffraction orders in each meridian, and wherein at least nine light spots are generated across the wavefront sensing unit in the two meridians.

7. A method for determining an ocular aberration of at least one eye of a user, the method comprising the following steps:
   a) measuring at least one optical wavefront comprised by at least one light beam, wherein an ocular aberration of the at least one eye of the user is determined from the at least one optical wavefront; and
   b) generating multiple diffraction orders in the at least one light beam in two meridians in a manner that the multiple diffraction orders are spatially separated on a wavefront sensing unit and in the at least one eye of the user,
wherein
the ocular aberration of the at least one eye of the user is determined by measuring at least one of a defocus of the at least one eye of the user or an equivalent sphere across a retinal field of the at least one eye of the user, wherein an ocular defocus map representing the ocular aberration of the retinal field in the at least one eye of the user is obtained, and wherein the ocular defocus map includes at least one of: values related to at least nine light spots generated across the wavefront sensing unit in the two meridians, or values interpolated between the at least nine light spots generated across the wavefront sensing unit.

8. The method according to claim 7, wherein
   a single diffractive element providing a two-dimensional grating is generating the multiple diffraction orders in the two meridians; or
   at least two individual diffractive elements are generating the multiple diffraction orders in one meridian, wherein the at least two individual meridians are arranged orthogonally with respect to each other; or
   at least one single diffractive element providing a one-dimensional grating is generating the multiple diffraction orders in one meridian, and is being rotated in a manner that the multiple diffraction orders are provided in the two meridians.

9. The method according to claim 7, wherein the ocular aberration of the at least one eye of the user is determined by measuring at least one of a defocus of the at least one eye of the user, or an equivalent sphere across a retinal field of the at least one eye of the user, and wherein an ocular defocus map representing the ocular aberration of the retinal field in the at least one eye of the user is obtained.

10. The method according to claim 7, wherein the multiple diffraction orders comprise at least a zeroth diffraction order and at least two first diffraction orders in each meridian, and wherein at least nine light spots are generated across the wavefront sensing unit in the two meridians.

11. The method according to claim 7, wherein at least one of a focus-adjustable fixation target and a pupil camera is placed in at least one additional optical path, and wherein the ocular defocus map is measured during an accommodation of the at least one eye of the user to the fixation target.

12. A method for producing at least one spectacle lens for at least one eye of a user, wherein the producing of the spectacle lens comprises processing a lens blank, wherein the processing of the lens blank is based on instructions configured to compensate at least one ocular aberration of the at least one eye of the user, and wherein the ocular aberration of the at least one eye is determined by the method for determining the ocular aberration of the at least one eye of the user according to claim 7.

13. A method for determining an ocular aberration of at least one eye of a user, the method comprising the following steps:
   a) measuring at least one optical wavefront comprised by at least one light beam, wherein an ocular aberration of the at least one eye of the user is determined from the at least one optical wavefront;
   b) generating multiple diffraction orders in the at least one light beam in two meridians in a manner that the multiple diffraction orders are spatially separated on a wavefront sensing unit and in the at least one eye of the user; and
   c) guiding the at least one light beam by at least one optical element to the at least one eye of the user and to a wavefront sensing unit, wherein the at least one optical element includes:
      a beam splitter configured to split the at least one light beam into at least two partial light beams, wherein at least one of the partial light beams is guided to the at least one eye of the user; and
      an optical relay system configured to relay an entrance pupil plane onto a pupil plane of the at least one eye of the user, wherein the at least one diffractive element is placed in the entrance pupil plane, and
   wherein
the beam splitter is placed in a manner that the same optical relay system is configured to relay the entrance pupil plane to a surface plane of the wavefront sensing unit.

14. The method according to claim 13, wherein
   a single diffractive element providing a two-dimensional grating is generating the multiple diffraction orders in the two meridians; or
   at least two individual diffractive elements are generating the multiple diffraction orders in one meridian, wherein the at least two individual meridians are arranged orthogonally with respect to each other; or
   at least one single diffractive element providing a one-dimensional grating is generating the multiple diffraction orders in one meridian, and is being rotated in a manner that the multiple diffraction orders are provided in the two meridians.

15. The method according to claim 13, wherein the ocular aberration of the at least one eye of the user is determined by measuring at least one of a defocus of the at least one eye of the user, or an equivalent sphere across a retinal field of the at least one eye of the user, and wherein an ocular defocus map representing the ocular aberration of the retinal field in the at least one eye of the user is obtained.

16. The method according to claim 13, wherein the multiple diffraction orders comprise at least a zeroth diffraction order and at least two first diffraction orders in each meridian, and wherein at least nine light spots are generated across the wavefront sensing unit in the two meridians.

17. The method according to claim 16, wherein the ocular defocus map comprises values related to the at least nine light spots generated across the wavefront sensing unit in the two meridians or values interpolated between the at least nine light spots generated across the wavefront sensing unit.

18. The method according to claim 13, wherein at least one of a focus-adjustable fixation target and a pupil camera is placed in at least one additional optical path, and wherein the ocular defocus map is measured during an accommodation of the at least one eye of the user to the fixation target.

19. A method for producing at least one spectacle lens for at least one eye of a user, wherein the producing of the spectacle lens comprises processing a lens blank, wherein the processing of the lens blank is based on instructions configured to compensate at least one ocular aberration of the at least one eye of the user, and wherein the ocular aberration of the at least one eye is determined by the method for determining the ocular aberration of the at least one eye of the user according to claim 13.

20. A method for determining an ocular aberration of at least one eye of a user, the method comprising the following steps:
   a) measuring at least one optical wavefront comprised by at least one light beam, wherein an ocular aberration of the at least one eye of the user is determined from the at least one optical wavefront; and
   b) generating multiple diffraction orders in the at least one light beam in two meridians in a manner that the multiple diffraction orders are spatially separated on a wavefront sensing unit and in the at least one eye of the user,
   wherein
the method further comprises providing an additional optical path, and wherein at least one of a fixation target and a pupil camera is placed in the additional optical path.

21. The method according to claim 20, wherein the ocular aberration of the at least one eye of the user is determined by measuring at least one of a defocus of the at least one eye of the user, or an equivalent sphere across a retinal field of the at least one eye of the user, and wherein an ocular defocus map representing the ocular aberration of the retinal field in the at least one eye of the user is obtained.

22. The method according to claim 20, wherein the multiple diffraction orders comprise at least a zeroth diffraction order and at least two first diffraction orders in each meridian, and wherein at least nine light spots are generated across the wavefront sensing unit in the two meridians.

23. The method according to claim 22, wherein the ocular defocus map comprises values related to the at least nine light spots generated across the wavefront sensing unit in the two meridians or values interpolated between the at least nine light spots generated across the wavefront sensing unit.

24. The method according to claim 20, wherein at least one of a focus-adjustable fixation target and a pupil camera are placed in at least one additional optical path, and wherein the ocular defocus map is measured during an accommodation of the at least one eye of the user to the fixation target.

25. A method for determining an ocular aberration of at least one eye of a user, the method comprising the following steps:
   a) measuring at least one optical wavefront comprised by at least one light beam, wherein an ocular aberration of the at least one eye of the user is determined from the at least one optical wavefront; and
   b) generating multiple diffraction orders in the at least one light beam in two meridians in a manner that the multiple diffraction orders are spatially separated on a wavefront sensing unit and in the at least one eye of the user,
   wherein
the method further comprises providing an additional optical path, and wherein at least one of a fixation target and a pupil camera is placed in the additional optical path, and wherein
   a single diffractive element providing a two-dimensional grating is generating the multiple diffraction orders in the two meridians; or
   at least two individual diffractive elements are generating the multiple diffraction orders in one meridian, wherein the at least two individual meridians are arranged orthogonally with respect to each other; or
   at least one single diffractive element providing a one-dimensional grating is generating the multiple diffraction orders in one meridian, and is being rotated in a manner that the multiple diffraction orders are provided in the two meridians.

26. A method for producing at least one spectacle lens for the at least one eye of a user, wherein the producing of the spectacle lens comprises processing a lens blank, wherein the processing of the lens blank is based on instructions configured to compensate at least one ocular aberration of the at least one eye of the user, and wherein the ocular aberration of the at least one eye is determined by a method for determining an ocular aberration of at least one eye of a user, the method comprising the following steps:
   c) measuring at least one optical wavefront comprised by at least one light beam, wherein an ocular aberration of the at least one eye of the user is determined from the at least one optical wavefront; and
   d) generating multiple diffraction orders in the at least one light beam in two meridians in a manner that the multiple diffraction orders are spatially separated on a wavefront sensing unit and in the at least one eye of the user,
   wherein
the method further comprises providing an additional optical path, and wherein at least one of a fixation target and a pupil camera is placed in the additional optical path.

* * * * *